(12) United States Patent
Gibson et al.

(10) Patent No.: US 7,540,206 B2
(45) Date of Patent: Jun. 2, 2009

(54) SELF-CLEANING SAMPLE EXTRACTION SYSTEM

(75) Inventors: James D. Gibson, Huntsville, AL (US); Frank A. Ruiz, Greenwell Springs, LA (US)

(73) Assignee: Parker-Hannifin Corporation, Cleveland, OH (US)

( * ) Notice: Subject to any disclaimer, the term of this patent is extended or adjusted under 35 U.S.C. 154(b) by 289 days.

(21) Appl. No.: 11/548,555

(22) Filed: Oct. 11, 2006

(65) Prior Publication Data

US 2007/0144274 A1 Jun. 28, 2007

Related U.S. Application Data

(60) Provisional application No. 60/736,484, filed on Nov. 14, 2005.

(51) Int. Cl.
*G01N 1/14* (2006.01)
*G01N 30/20* (2006.01)
(52) U.S. Cl. .................. 73/864.62; 73/23.41; 73/31.07; 73/863.24
(58) Field of Classification Search ............. 73/864.62, 73/863.24, 23.41, 31.07, 863.84, 863.86, 73/863.02, 863.03, 64.56
See application file for complete search history.

(56) References Cited

U.S. PATENT DOCUMENTS 4,527,436 A 7/1985 Jones

| | | | |
|---|---|---|---|
| 5,587,525 A * | 12/1996 | Shwe et al. ............... | 73/152.52 |
| 5,736,654 A | 4/1998 | Dubois | |
| 6,432,630 B1 * | 8/2002 | Blankenstein .................. | 435/4 |
| 6,899,315 B2 | 5/2005 | Maiville et al. | |

* cited by examiner

*Primary Examiner*—Thomas P Noland
(74) *Attorney, Agent, or Firm*—Renner, Otto, Boisselle & Sklar LLP

(57) ABSTRACT

A sampling apparatus for use with a sample analyzer comprises a sample probe insertable into a process stream, and an extraction cylinder including a variable volume chamber and a piston movable by an actuator back and forth in the cylinder to increase and decrease the volume of the variable volume chamber. A sampling valve is connected between the extraction cylinder and the sample probe, with a sample line connecting the sampling valve to the sample probe, and the variable volume chamber having a capacity substantially greater than the combined volumes of the sample probe, sampling valve and sample line. A filter assembly is interposed between the sample probe and sampling valve for filtering undesired substances from the fresh sample prior to the fresh sample reaching the sampling valve, and a controller is provided for controlling the actuator and the sampling valve, first to move the piston at a first rate to increase the variable volume chamber sufficiently to draw fresh sample from the process stream and past the sampling valve, then to operate the sampling valve for injecting fresh sample into the sample analyzer, and thereafter to move the piston at a second rate greater than the first rate to decrease the variable volume chamber to flush excess sample back into the process stream and clean the filter of undesired substances filtered from the fresh sample.

23 Claims, 5 Drawing Sheets

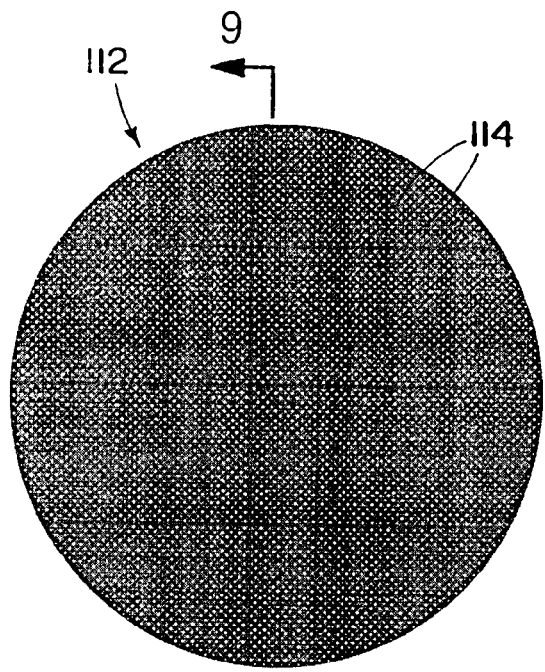
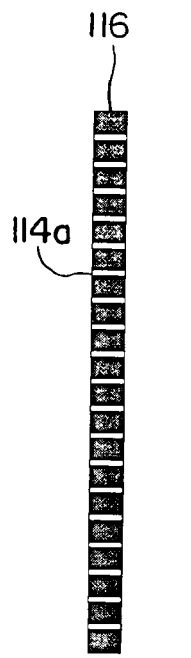
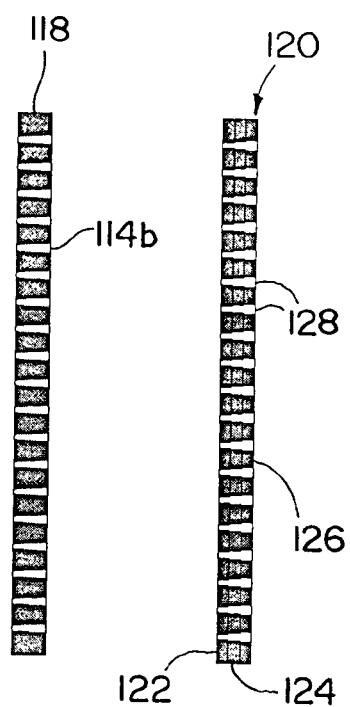
FIG. 8  FIG. 9  FIG. 10
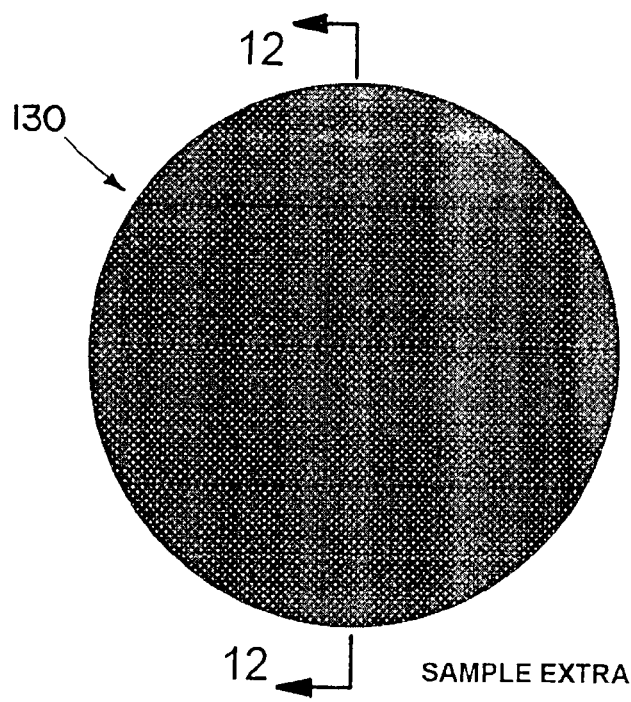
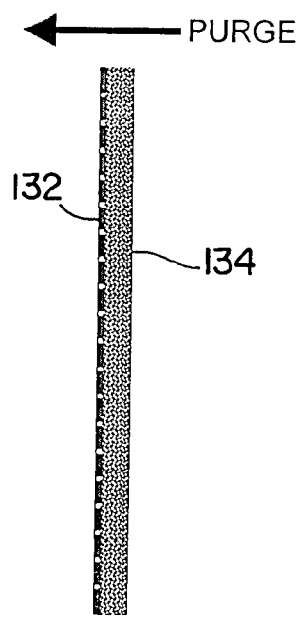
FIG. 11  FIG. 12

SELF-CLEANING SAMPLE EXTRACTION SYSTEM

RELATED APPLICATIONS

This application claims the benefit of U.S. Provisional Application No. 60/736,484; filed Nov. 14, 2005, which is hereby incorporated herein by reference.

FIELD OF THE INVENTION

The invention herein described relates generally to a self-contained on-line sampling apparatus that returns a sample after testing to the process stream and which has a self-cleaning feature.

BACKGROUND

On-line analysis of process streams is used for a variety of reasons, including process control and quality assurance. Typically a sample is withdrawn from the process stream and injected by a sampling valve into an analytical instrument. In many online sampling apparatus the sample is discarded and this may present an environmental issue depending on the nature of the sample. In some systems, provision is made for reintroducing the sample back into the process stream, but these systems may be plagued by sample contamination. Another problem is that filters used to filter a sample taken from a process stream become clogged, requiring frequent replacement and/or cleaning.

SUMMARY OF THE INVENTION

The present invention provides a sampling apparatus that affords one or more advantages including, in particular, self-cleaning when excess sample is flushed back into the process stream from which the sample was taken. The present invention also provides a novel filter assembly that reduces clogging and facilitates cleaning of the filter during back flushing of sample therethrough.

Accordingly, a sampling apparatus for use with a sample analyzer comprises a sample probe insertable into a process stream, and an extraction cylinder including a variable volume chamber and a piston movable by an actuator back and forth in the cylinder to increase and decrease the volume of the variable volume chamber. A sampling valve is connected between the extraction cylinder and the sample probe, with a sample line connecting the sampling valve to the sample probe, and the variable volume chamber having a capacity greater than the combined volumes of the sample probe, sampling valve and sample line, whereby fresh sample can be drawn from the process stream and past the sampling valve by moving the piston to increase the variable volume chamber, so that fresh sample within the sampling valve can be injected into a sample analyzer. A filter assembly is interposed between the sample probe and sampling valve for filtering undesired substances from the fresh sample prior to the fresh sample reaching the sampling valve; and a controller is provided for controlling the actuator and the sampling valve, first to move the piston at a first rate to increase the variable volume chamber sufficiently to draw fresh sample from the process stream and past the sampling valve, then to operate the sampling valve for injecting fresh sample into the sample analyzer, and thereafter to move the piston at a second rate greater than the first rate to decrease the variable volume chamber to flush excess sample back into the process stream and clean the filter of undesired substances filtered from the fresh sample.

According to another aspect of the invention, the filter assembly comprises a filter housing including an interior filter chamber connected between inlet and outlet passages, and a filter within the filter chamber. The filter has a cross-sectional flow-through area greater than the cross-sectional flow area of at least the inlet passage whereby fresh sample drawn from the probe and through the filter assembly will flow through the first filter at a rate less than flow through the inlet passage, thereby reducing the speed at which undesired particulate substances carried by the fresh sample will impact the first filter and thus reduce the degree to which such particulate substances may become imbedded in the first media.

The filter assembly may also comprise a second more fragile filter in series with the first filter for filtering an undesirable fluid or fluids from the fresh sample drawn through the filter assembly. The filter assembly may also include a bypass passage for allowing sample to flow around the second filter, and a check valve for blocking forward flow through the bypass passage while permitting reverse flow through the bypass passage when excess sample is back flushed through the filter assembly. The bypass passage may communicate with an inlet side of the second filter through radially directed nozzles that operate during back flushing to accelerate and direct flow of the excess sample across the inlet side of the second filter, thereby to assist in dislodging and flushing away of unwanted substances captured by the second filter. The bypass passage may communicate with an outlet side of the second filter through radially extending passages, and the check valve may include an elastomeric O-ring surrounding and closing radially outer ends of the radially extending passages, the O-ring blocking flow through the radially extending passages from the inlet to the outlet, and being displaceable radially outwardly by fluid pressure to permit flow from the outlet to the inlet via the bypass passage.

The second filter may be a membrane filter supported on the outlet side thereof by a support structure, such as a sintered metal filter.

The first filter may be a metallic filter. More particularly, the first filter may include a series of through holes that over at least a portion thereof decrease in width going from an inlet side to an outlet side of the first filter. The through holes may be tapered inwardly going from the outlet side to the inlet side. In an alternative arrangement, the first filter may include multiple layers each containing respective portions of the through holes, which portions are of uniform width through each layer and which from layer to layer increase in width going from the inlet side to the outlet side of the first filter. In a further arrangement, the first filter may include an inlet side layer and an outlet side layer, the outlet side layer being a sintered metal or ceramic filter and the inlet side layer including a plurality of axially extending through holes of uniform or tapered width.

According to another aspect of the invention, a sampling method comprises the steps of moving a piston at a first rate to increase a variable volume chamber sufficiently to draw fresh sample from a process stream, through a filter and past a sampling valve, then operating the sampling valve for injecting fresh sample into a sample analyzer, and thereafter moving the piston at a second rate greater than the first rate to decrease the variable volume chamber to flush excess sample back into the process stream and clean a filter of undesired substances filtered from the fresh sample during sample extraction.

Further features of the invention will become apparent from the following detailed description when considered in conjunction with the drawings.

BRIEF DESCRIPTION OF THE DRAWINGS

In the annexed drawings,

FIG. 8 is an axial end view of a particle filter element used in a filter assembly of FIG. 6;

FIG. 9 is an exploded cross-sectional view of the particle filter element of FIG. 8;

FIG. 10 is a cross-sectional view of another particle filter element useful in the filter assembly of FIG. 6;

FIG. 11 is an axial end view of still another particle filter element useful in a filter assembly of FIG. 6;

FIG. 12 is a cross-sectional view of the particle filter element of FIG. 11.

DETAILED DESCRIPTION

Figure 1:
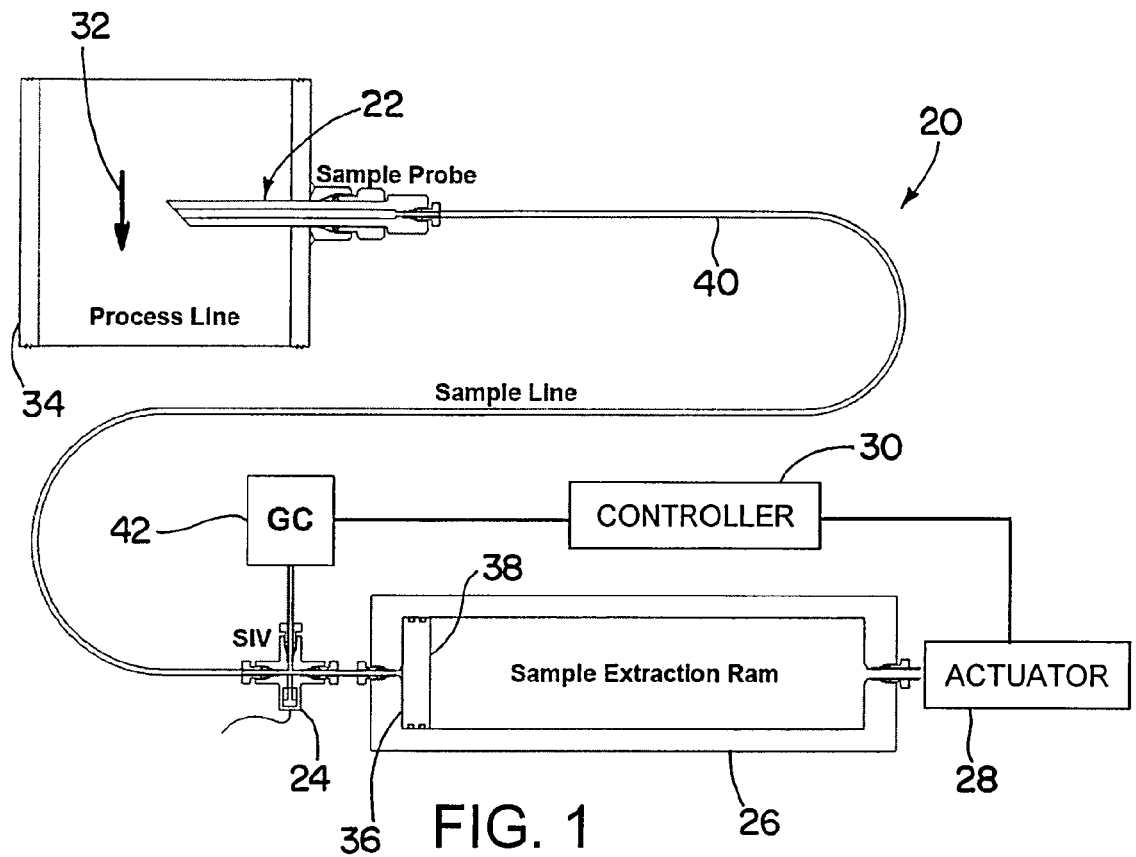
FIG. 1 is a schematic illustration of an exemplary sampling apparatus according to the invention.

Referring now in detail to the drawings and initially to FIG. 1, an exemplary sampling apparatus according to the invention is generally designated by reference numeral 20. The apparatus 20 generally comprises a sample probe 22, a sampling valve 24, an extraction cylinder 26, an actuator 28 and a controller 30. The sample probe is insertable into a process stream 32 flowing through a conduit 34. The extraction cylinder 26, also herein referred to as a sample extraction ram (SER), includes a variable volume chamber 36 and a piston 38 movable by the actuator 28 back and forth in the cylinder to increase and decrease the volume of the variable volume chamber. The sampling valve 24 is connected between the extraction cylinder and the sample probe, with a sample line 40 connecting the sampling valve to the sample probe. The variable volume chamber having a capacity substantially greater than the combined volumes of the sample probe, sampling valve and sample line, whereby fresh sample can be drawn from the process stream and past the sampling valve by moving the piston to increase the variable volume chamber. Fresh sample within the sampling valve can then be injected into a sample analyzer 42.

Figure 2:
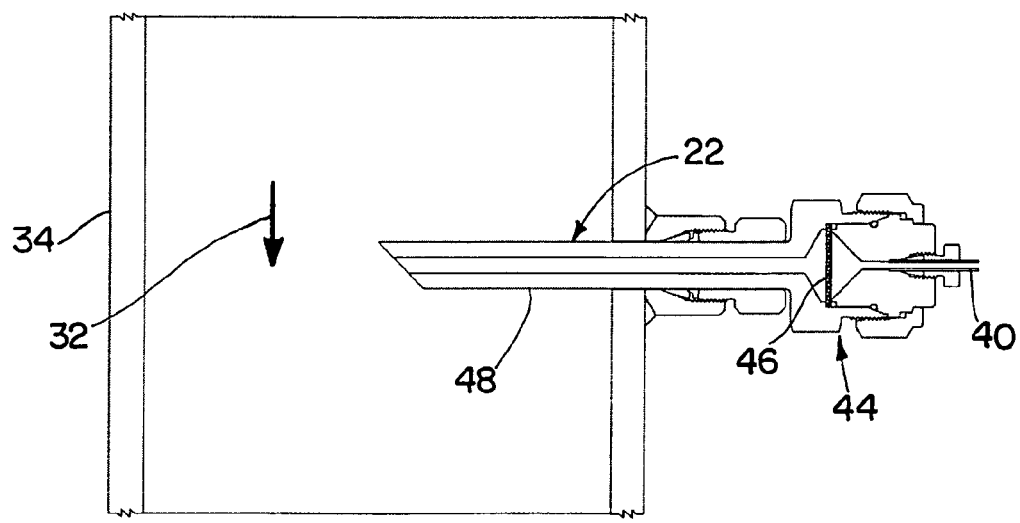
FIG. 2 is a cross-sectional view of a sample probe used in the sampling apparatus of FIG. 1, shown in relation to a conduit containing a process stream.

As illustrated in FIG. 2, the apparatus 20 may be provided with a filter assembly 44 that is interposed between the sample probe 22 and the sampling valve 24 for filtering undesired substances from the fresh sample prior to the fresh sample reaching the sampling valve. The filter assembly shown in FIG. 2 includes a porous flow-through filter element 46.

Figure 3:
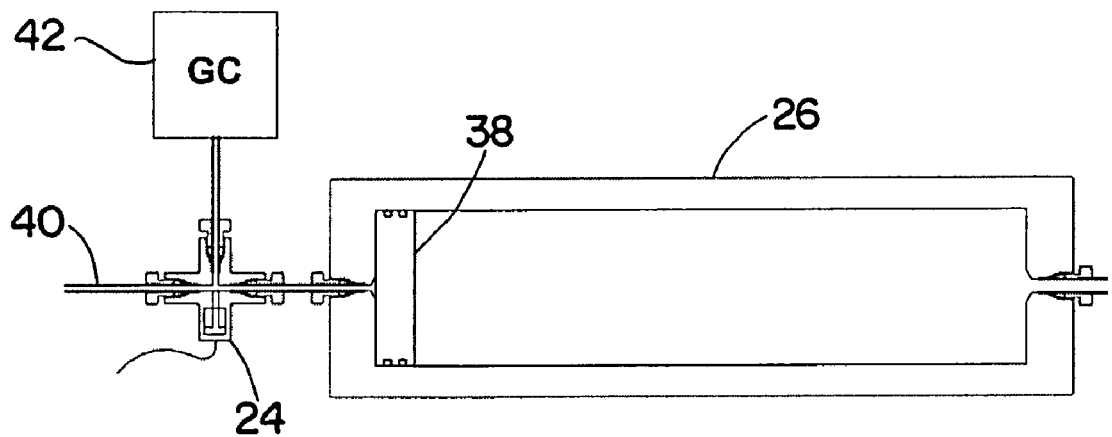
FIGS. 3-5 are sequential cross-sectional views of a hydraulic cylinder and piston assembly used in the sampling apparatus, with the piston shown in different positions during sample extraction.
Figure 4:
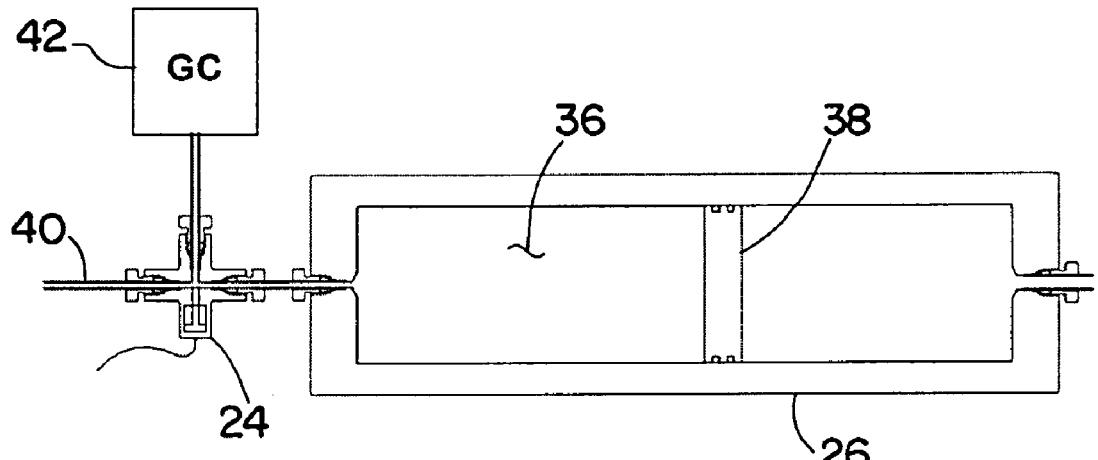
Figure 5:
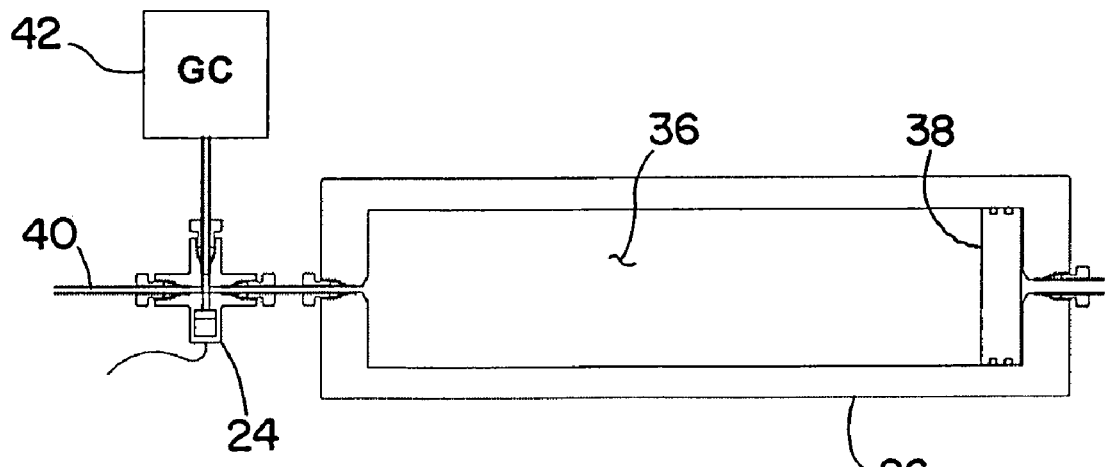

As discussed further below, the controller 30 controls the actuator 28 and the sampling valve 24, first to move the piston 38 at a first rate to increase the variable volume chamber 36 as illustrated in FIGS. 3-5 sufficiently to draw fresh sample from the process stream and past the sampling valve, then to operate the sampling valve for injecting fresh sample into the sample analyzer 42. Thereafter, the controller controls the actuator so as to move the piston in the opposite direction at a second rate greater than the first rate to decrease the variable volume chamber and flush excess sample back into the process stream 32 and further clean the filter assembly 44 of undesired substances that had been filtered from the fresh sample during the sample extraction.

More particularly, the SER 26 first retracts slowly to extract fresh sample from the process stream 32 through the sample probe 22, the sample line 40 and the sampling valve 24. Second, the sampling valve directs fresh sample into the sample analyzer 42 for analysis. Third, the SER extends rapidly to flush excess sample back into the process pipe line 34. This procedure eliminates the need to flare or otherwise dispose of the excess sample. This can also eliminate the need for a fast loop line to bring sample close to the sample analyzer, which is required by some prior art systems.

The sampling valve 24 may be of any suitable type for transferring a sample of the process stream to the sample analyzer 42. In particular, the sampling valve may be a sample injection valve (SIV), which are well known in the art.

The sample analyzer likewise can be of any suitable type, such as, for example, a gas chromatograph (GC).

As seen in FIG. 2, the sample probe 22 may include a tubular member 48 that may have a small internal diameter to minimize sample volume and thus system response time, and further to increase the strength of the tubular member against process stream flow, corrosion and/or entrained objects. The tubular member may have an angled end pointed away from the flow direction to help prevent clogging from particles suspended in the stream. The sample line 40 may be connected to the sample probe, although preferably the sample line is connected to the filter assembly 44 that in turn is connected to the sample probe. The filter assembly 44 may be integrated with the sample probe to provide a filtered sample probe as shown or may be placed anywhere along the sample line before SIV 24 for better accessibility and maintenance.

The sample line 40 is connected between the probe and the sample injection valve 24. The sample line can be quite long but preferably the sample line is kept as short as possible to minimize pressure loss and the total volume of sample extracted from the process stream 32.

During the first stage of sample extraction, fresh sample can be slowly extracted through the probe 22 by slowly moving the piston 38 from its position shown in FIG. 3 to its position shown in FIG. 4 and then to a fully retracted position shown in FIG. 5. The filter assembly 44 will separate suspended particles from the sample media and fresh clean media will continue down the sample line 40. The controller can be programmed to limit the sample velocity in high pressure systems and thus minimize the speed and force that particles may impact and become lodged in the flow-through filter element 46 of the filter assembly 44. In low pressure systems, the extraction ram 26 can provide additional suction to speed fresh media down the sample line 40. This will reduce lag time for fresh media to the analyzer 42 and allow for smaller sample lines and sample volumes.

As the piston is being retracted, all of the old sample media will be extracted from the sample line and replaced by fresh sample media. This may occur, for example, during the first half or third of the ram stroke, or less. Then, continued movement of the piston will continue to flush the sample line with fresh sample to insure accurate sample quality in the sample line and at the sampling valve.

While the extraction stoke is slow to keep particles from lodging deeply in the filter element of the filter assembly, the return stroke from the FIG. 5 position to the FIG. 3 position preferably is fast and can even be pulsated under the control of the controller to dislodge particles from the filter media and thereby clean the filter media, with the unused sample being flushed back into the process stream. At the end of the stroke, all clean excess sample is flushed back into the process stream and the filter probe is cleaned. In this controlled two stroke process, the filter element is back flushed or cleaned after every sample extraction. This can greatly reduce system maintenance, down time and costs to replace and/or clean the filter element or elements.

Figure 6:
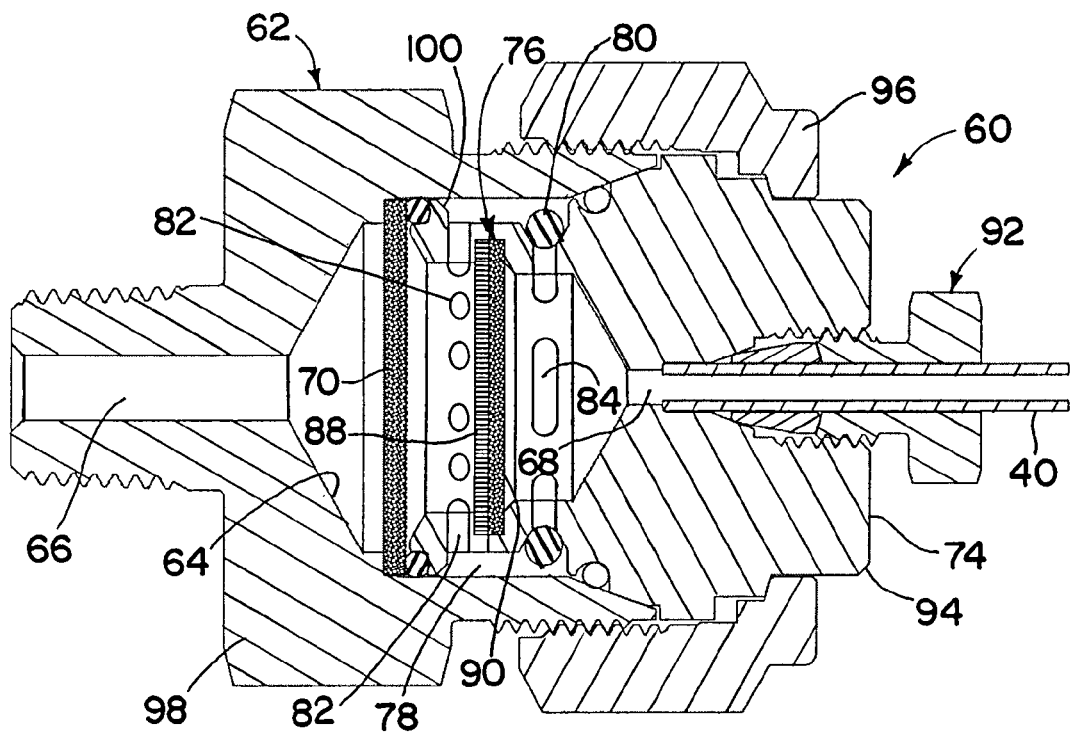
FIG. 6 is cross-sectional view of a filter assembly employed in the sampling apparatus.

Referring now to FIG. 6, another filter assembly useful in the sampling apparatus 20 is indicated generally at 60. The filter assembly 60 comprises a filter housing 62 including an interior filter chamber 64 connected between inlet and outlet passages 66 and 68, and a first filter element 70 within the filter chamber 64. The filter element 70 has a cross-sectional flow-through filtration area greater than the cross-sectional flow area of at least the inlet passage 66 whereby fresh sample drawn through the filter assembly will flow through the first filter element at a rate less than the rate of flow through the inlet passage 66. This reduces the speed and force at which undesired particulate substances carried by the fresh sample will impact the first filter element and thus reduce the degree to which such particulate substances may become imbedded in the first filter element.

The filter assembly 60 may also comprise a second membrane filter element 76 in series with the first filter element 70 for filtering an undesirable fluid or fluids from the fresh sample drawn through the filter assembly. The filter assembly may also include a bypass passage 78 for allowing sample to flow around the second filter element, and a check valve member 80 for blocking forward flow through the bypass passage 78 while permitting reverse flow through the bypass passage when excess sample is back flushed through the filter assembly. The bypass passage 78 may communicate with an inlet side of the second filter element 76 through radially directed nozzles 82, also herein referred to as orifices, that operate during back flushing to accelerate and direct flow of the excess sample across the inlet side of the second filter. This assists in dislodging and flushing away of unwanted substances captured by the second filter element. That is, the outlet orifices direct flow across the surface of the membrane filter to sweep isolated droplets off the face of the membrane and back through the metal filter on the left and into the process stream. Back flushing of the isolated droplets is further facilitated by a slight back flow of clean media through the membrane filter.

The bypass passage 78 may communicate with an outlet side of the second filter element through radially extending passages 84, and the check valve member 80 may include an elastomeric O-ring or similarly expanding check element surrounding and/or closing radially outer ends of the radially extending passages 84. As seen in FIG. 6, the O-ring closes and thus blocks flow through the radially extending passages 84 from the filter inlet to the filter outlet. When flow is reversed during back flushing, fluid pressure will cause the O-ring to expand and move away from the passages 84, for flow from the outlet to the inlet via the bypass passage 78. The O-ring check valve can open at a very low differential pressure to almost equalize the pressure across the membrane filter element 76 and protect it from during the fast back flush.

The second filter element 76 may be a composite including a porous membrane 88 that is supported at its outlet side by a support structure 90, such as a sintered metal disk. The porous membrane filter functions to restrict flow of selected liquids (e.g. water).

Figure 7:
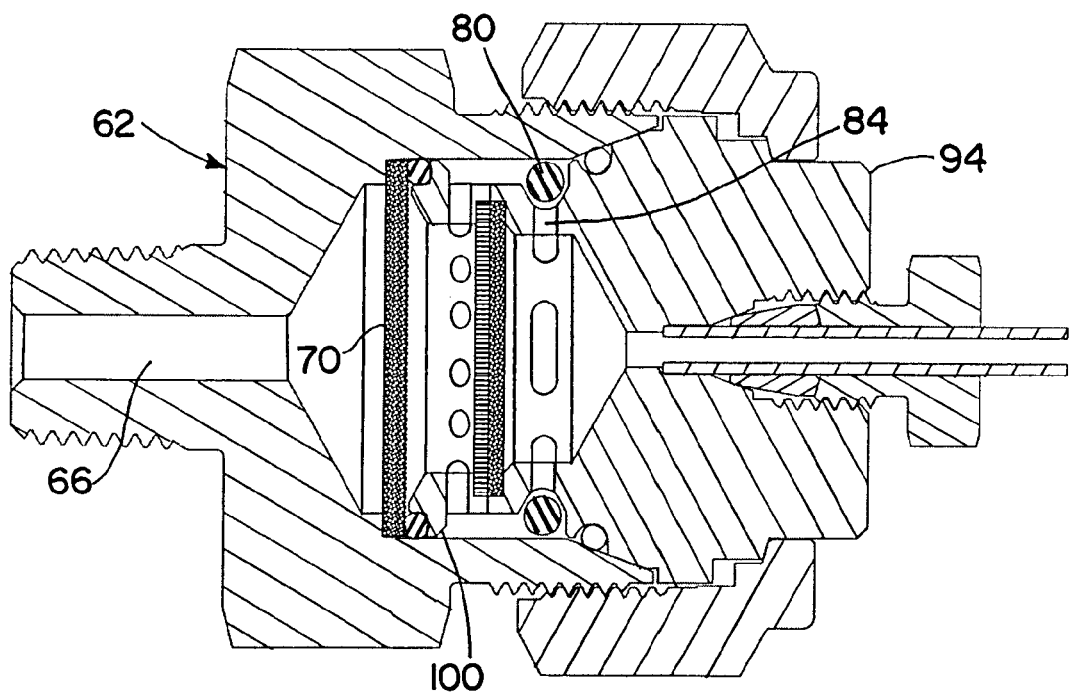
FIG. 7 is a view similar to FIG. 6, but showing a check valve member unseated during back flushing of the filter assembly.

The first filter element 70 may be a metallic filter as shown in FIGS. 6 and 7.

Before leaving FIG. 6, it is noted that a small inverted tube fitting connection 92 provides for connection of the sample tube 40 to the housing 62. The tube fitting connection is integral to the filter cap 94 to minimize sample volume and protect the tube connection. The filter cap 94 is held in place by suitable means such as a nut 96 threaded onto the main body 98 of the housing 62. Sandwiched between the filter cap and an annular shoulder on the main body 98, going from left to right in FIG. 6, are the first filter element 70, seal retainer and spacer member 100, and the second filter element 76. Thus, when the cap is removed, the filter elements can be easily accessed for service and/or replacement.

In FIGS. 8 and 9, another first filter element 112 can be seen to include a series of through holes 114 that over at least a portion thereof increase in width (diameter) going from an inlet side to an outlet side of the first filter (left to right in FIG. 9). The through holes may be flared outwardly going from the inlet side to the outlet side all the way through the filter element or, as shown, the first filter may include multiple layers 116 and 118 each forming respective portions 114a and 114b of the through holes 114. The hole portions 114a in the inlet side layer 116 may be of uniform width whereas the hole portions 114b in the outlet side layer 118 increase in width going from the inlet side to the outlet side. The illustrated columnar hole filter serves as a filter to stop particles while reducing the number of particles that become permanently trapped in the filter. The columnar holes also better facilitate the back flushing of the filter to a virtually clean condition.

In FIG. 10, there is shown another first filter element 120. The filter element 120 includes multiple layers 122, 124 and 126 (three shown) each containing respective portions of through holes 128. The portion of each through hole in each layer is of uniform width through the layer, but from layer to layer such portions of each through hole increase in width going from the inlet side to the outlet side of the first filter.

In FIGS. 11 and 12, there is shown still another exemplary filter element 130. The filter element 130 includes an inlet side layer 132 and an outlet side layer 134. The outlet side layer 134 may be a sintered metal or ceramic filter and the inlet side layer 132 may include a plurality of axially extending through holes of uniform or tapered width, like those above describe in connection with FIGS. 8-10.

Figure 13:
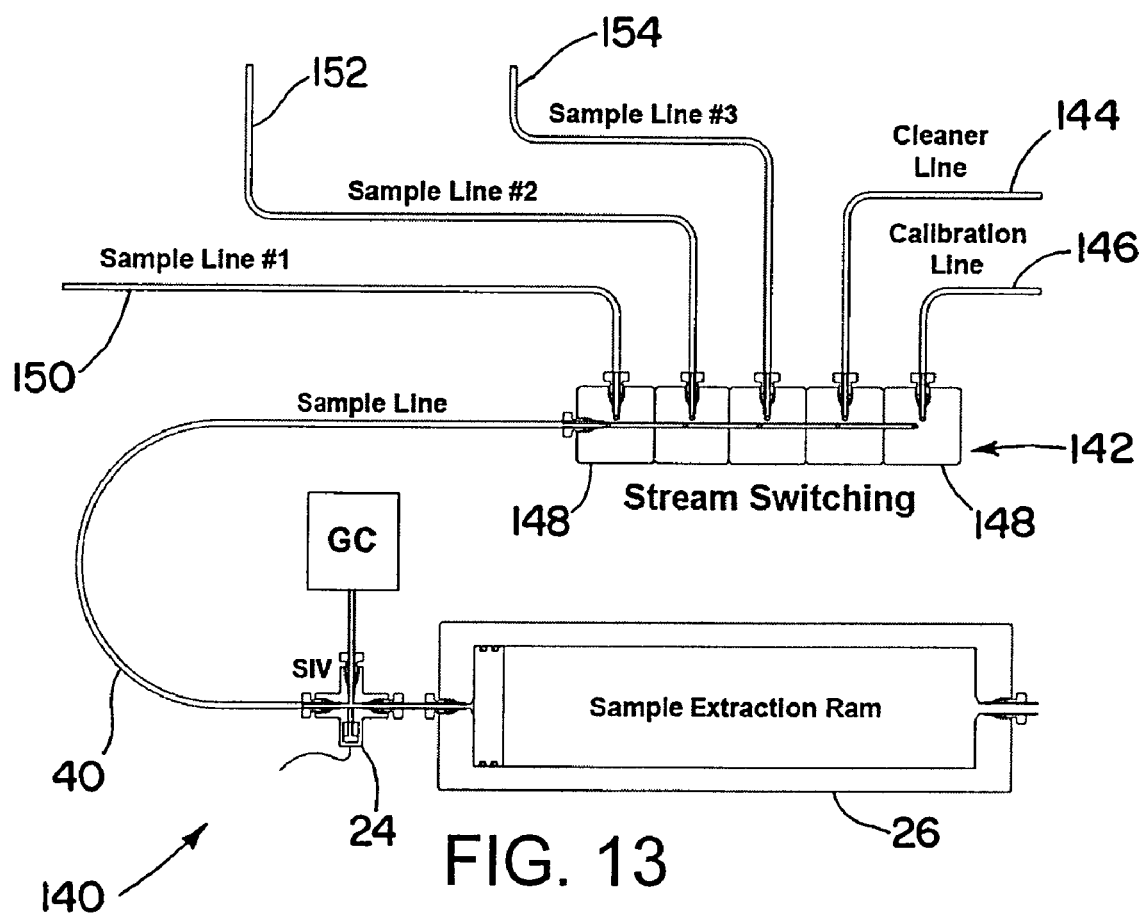
FIG. 13 is another exemplary sampling apparatus according to the invention.

As will be appreciated, the various features of the above-described sampling apparatus may be used separately or in different arrangements and/or combinations. This is illustrated in FIG. 13 which shows another exemplary sampling apparatus 140 according to the invention. The sampling apparatus 140 includes a sampling valve 24, extraction ram 26 and sample analyzer 42 like the apparatus of FIG. 1. The sample line 40, however, is not connected to a single sample probe, but instead is connected to a stream switching device 142. When used with a stream switching device, one SER 26 can be used to extract samples from multiple process lines. The stream switching device 142 also can allow injection of special flushing media via cleaner line 144 as needed to clean sample lines, probes and filters. The stream switching device 142 can also be used to automatically inject previously analyzed samples for calibration via a calibration line 146. The stream switching device is provided with suitable valves 148 for selectively connecting the common sample line 40 to one or more sample lines 150, 152 and 154 connected to respective sampling probes (not shown), the cleaner line 144 and the calibration line 146.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A sampling apparatus for use with a sample analyzer, comprising:
    a sample probe insertable into a process stream;
    an extraction cylinder including a variable volume chamber and a piston movable by an actuator back and forth in the cylinder to increase and decrease the volume of the variable volume chamber;
    a sampling valve connected between the extraction cylinder and the sample probe, with a sample line connecting the sampling valve to the sample probe, and the variable volume chamber having a capacity greater than the combined volumes of the sample probe, sampling valve and sample line, whereby fresh sample can be drawn from the process stream and past the sampling valve by moving the piston to increase the variable volume chamber, so that fresh sample within the sampling valve can be injected into a sample analyzer;
    a filter assembly interposed between the sample probe and sampling valve for filtering undesired substances from the fresh sample prior to the fresh sample reaching the sampling valve; and
    a controller for controlling the actuator and the sampling valve, first to move the piston at a first rate to increase the variable volume chamber sufficiently to draw fresh sample from the process stream and past the sampling valve, then to operate the sampling valve for injecting fresh sample into the sample analyzer, and thereafter to move the piston at a second rate greater than the first rate to decrease the variable volume chamber to flush excess sample back into the process stream and clean the filter of undesired substances filtered from the fresh sample.

2. A sampling apparatus according to claim 1, wherein the filter assembly comprises a filter housing including an interior filter chamber connected between inlet and outlet passages, and a first filter within the filter chamber, the first filter having a cross-sectional flow-through area greater than the cross-sectional flow area of at least the inlet passage whereby fresh sample drawn from the probe and through the filter assembly will flow through the first filter at a rate less than flow through the inlet passage, thereby reducing the speed at which undesired particulate substances carried by the fresh sample will impact the first filter and thus reduce the degree to which such particulate substances may become imbedded in the first media.

3. A sampling apparatus according to claim 2, wherein the filter assembly further comprises a second filter in series with the first filter for filtering an undesirable fluid or fluids from the fresh sample drawn through the filter assembly.

4. A sampling apparatus according to claim 3, wherein the filter assembly includes a bypass passage for allowing sample to back flow around the second filter, and a check valve for blocking forward flow through the bypass passage while permitting reverse flow through the bypass passage when excess sample is back flushed through the filter assembly.

5. A sampling apparatus according to claim 4, wherein the bypass passage communicates with an inlet side of the second filter through radially directed nozzles that operate during back flushing to accelerate and direct flow of the excess sample across the inlet side of the second filter, thereby to assist in dislodging and flushing away of unwanted substances captured by the second filter.

6. A sampling apparatus according to claim 4, wherein the bypass passage communicates with an outlet side of the second filter through radially extending passages, and the check valve includes an elastomeric annulus surrounding and closing radially outer ends of the radially extending passages, the annulus blocking flow through the radially extending passages from the inlet to the outlet, and being displaceable radially outwardly by fluid pressure to permit flow from the outlet to the inlet via the bypass passage.

7. A sampling apparatus according to claim 3, wherein the second filter is a membrane filter.

8. A sampling apparatus according to claim 7, wherein the support structure is a sintered metal filter.

9. A sampling apparatus according to claim 3, wherein the first filter is a metallic or ceramic filter.

10. A sampling apparatus according to claim 3, wherein the first filter includes a series of through holes that over at least a portion thereof decrease in width going from an inlet side to an outlet side of the first filter.

11. A sampling apparatus according to claim 10, wherein the through holes are tapered inwardly going from the outlet side to the inlet side.

12. A sampling apparatus according to claim 10, wherein the first filter includes multiple layers each containing respective portions of the through holes, which portions are of uniform width through each layer and which from layer to layer increase in width going from the inlet side to the outlet side of the first filter.

13. A sampling apparatus according to claim 3, wherein the first filter includes an inlet side layer and an outlet side layer, the outlet side layer being a sintered metal or ceramic filter and the inlet side layer including a plurality of axially extending through holes of uniform or tapered width.

14. A sampling apparatus according to claim 1, in combination with the sample analyzer.

15. A sampling apparatus combination according to claim 14, wherein the filter assembly comprises
    a filter housing including an interior filter chamber connected between inlet and outlet passages, and
    a first filter within the filter chamber, the first filter having a cross-sectional flow-through area greater than the cross-sectional flow area of at least the inlet passage whereby fresh sample drawn through the filter assembly will flow through the first filter at a rate less than flow through the inlet passage, thereby reducing the speed at which undesired particulate substances carried by the fresh sample will impact the first filter and thus reduce the degree to which such particulate substances may become imbedded in the first media.

16. A combination according to claim 15, wherein the filter assembly further comprises a second filter in series with the first filter for filtering an undesirable fluid or fluids from the fresh sample drawn through the filter assembly.

17. A combination according to claim 16, wherein the second filter is a membrane filter.

18. A combination according to claim 15, wherein the filter assembly includes a bypass passage for allowing sample to flow around the second filter, and a check valve for blocking forward flow through the bypass passage while permitting reverse flow through the bypass passage when excess sample is back flushed through the filter assembly.

19. A combination according to claim 18, wherein the bypass passage communicates with an inlet side of the second filter through radially directed nozzles that operate during back flushing to accelerate and direct flow of the excess sample across the inlet side of the second filter, thereby to assist in dislodging and flushing away of unwanted substances captured by the second filter.

20. A combination according to claim 18, wherein the bypass passage communicates with an outlet side of the second filter through radially extending passages, and the check valve includes an elastomeric annulus surrounding and closing radially outer ends of the radially extending passages, the annulus blocking flow through the radially extending passages from the inlet to the outlet, and being displaceable radially outwardly by fluid pressure to permit flow from the outlet to the inlet via the bypass passage.

21. A combination according to claim 15, wherein the first filter includes a series of through holes that over at least a portion thereof increase in width going from an inlet side to an outlet side of the first filter.

22. A combination according to claim 21, wherein the first filter includes multiple layers each containing respective portions of the through holes, which portions are of uniform width through each layer and which from layer to layer increase in width going from the inlet side to the outlet side of the first filter.

23. A combination according to claim 15, wherein the first filter includes an inlet side layer and an outlet side layer, the outlet side layer being a sintered metal or ceramic filter and the inlet side layer including a plurality of axially extending through holes of uniform or tapered width.

\* \* \* \* \*